(12) United States Patent
Hooper

(10) Patent No.: US 7,566,328 B2
(45) Date of Patent: Jul. 28, 2009

(54) ANATOMICAL APRON AND METHOD FOR ILLUSTRATING SURGICAL PROCEDURES

(76) Inventor: Donna Joy Hooper, 2612 Tyson Ave., Tifton, GA (US) 31794

( * ) Notice: Subject to any disclaimer, the term of this patent is extended or adjusted under 35 U.S.C. 154(b) by 191 days.

(21) Appl. No.: 10/964,152

(22) Filed: Oct. 13, 2004

(65) Prior Publication Data

US 2006/0079855 A1 Apr. 13, 2006

(51) Int. Cl.
*A61B 19/00* (2006.01)
*A41B 13/10* (2006.01)
*G09B 11/00* (2006.01)
*G09B 23/28* (2006.01)
*G09B 25/00* (2006.01)

(52) U.S. Cl. .............................. 604/357; 2/48; 434/86; 434/267; 434/395

(58) Field of Classification Search ................. 604/357; 2/48, 49.1, 49.2, 49.3, 49.4, 49.5, 50, 51; D2/740, 775, 860–864; 434/86, 267, 272, 434/395, 396
See application file for complete search history.

(56) References Cited

U.S. PATENT DOCUMENTS

| | | | | |
|---|---|---|---|---|
| 4,231,119 A * | 11/1980 | Quinn | ............................. | 2/48 |
| 4,710,979 A * | 12/1987 | Bull et al. | ........................ | 2/48 |
| 5,201,073 A * | 4/1993 | Spanier | ........................ | 2/49.2 |
| 5,468,152 A * | 11/1995 | Lenart | ........................ | 434/429 |
| 5,718,589 A * | 2/1998 | McCracken et al. | ......... | 434/159 |
| 5,933,866 A * | 8/1999 | Fox | ................................ | 2/115 |
| 6,085,356 A * | 7/2000 | Redmond, Sr. | ................. | 2/237 |
| 6,360,372 B2 * | 3/2002 | Oster | ............................ | 2/126 |
| 2002/0108162 A1* | 8/2002 | Bolds-Leftridge | ............ | 2/49.1 |
| 2005/0278825 A1* | 12/2005 | Altman | ........................ | 2/115 |

OTHER PUBLICATIONS

Disposable Anatomical Aprons; www1.fishersci.com.*
Medical School T-Shirts; http://www.web.archive.org/web/20020623132855/http://anatomy-resources.com/human-anatomy/sh931.htm; Jun. 23, 2002.*
Skeleton; www.shockingfun.com; Jun. 27, 2004.*
Gut Feeling; SideShow—the Exhibits, p. 2; www.questacon.edu.au/html/sideshow_the_exhibits.html.*
Anatomy Apron; http://web.archive.org/web/20031130020802/http://edushop.edu4kids.com/catalog/product_info.php?products_id=1462; Nov. 30, 2003.*
"Anatomy Apron," http://edushop.edu4kids.com/catalog/product_info.php?products_id=1462, visited Jan. 13, 2005 (2 pages).
"Maggie Apron," http://www.joicfp.or.jp/eng/audio_visual/maggie.html, visited Jan. 13, 2005 (1 page).
"Arin Apron Model," http://www.mkupdate.co.uk/acatalog/Torso.html, visited Jan. 13, 2005 (5 pages).
International Search Report.
http://www.edushop.edu4kids.com/catalog/product_info.php?products_id=1462 (Edushop) Jul. 18, 2003.

* cited by examiner

*Primary Examiner*—Tatyana Zalukaeva
*Assistant Examiner*—Michael G Bogart
(74) *Attorney, Agent, or Firm*—Thomas, Kayden, Horstemeyer & Risley, LLP

(57) ABSTRACT

An anatomical apron configured for illustrating an ostomy surgical procedure is provided. The apron includes a body portion having a neck loop attached thereto that is configured to loop around a person's neck so that the body portion covers a frontal area of the person's body. The apron includes one or more pieces of material fashioned as human body organs fastened to the apron body. A first flap is attached to the apron body and configured to cover a portion of the one or more pieces of material fashioned as body organs, wherein the first flap may be fastened in a covered position. The apron also includes one or more slits positioned in the first flap configured such that one or more of the pieces of material fashioned as human body organs may be routed through so as to illustrate a surgical procedure.

20 Claims, 6 Drawing Sheets

ANATOMICAL APRON AND METHOD FOR ILLUSTRATING SURGICAL PROCEDURES

FIELD OF THE INVENTION

This disclosure generally relates to anatomical illustrations, and more particularly, to an apron and method for illustrating physiologic structural alterations related to surgical procedures.

BACKGROUND OF THE INVENTION

Many people are often reluctant and/or have a distinct fear of going to a doctor or physician. Medical procedures for even routine and common ailments and conditions may oftentimes be intrusive, uncomfortable, and generally unfavorable to the patient. For more complicated procedures, many people oftentimes dread going to a doctor due to the uncertainty of the medical procedures to be performed.

With the advent of medical related technologies, physicians are able to diagnose and treat medical conditions for diseases and ailments that previously could not be treated. Moreover, for other conditions, processes, and techniques have been developed that enable physicians to treat patients in new ways in all parts of the body. However, the additional complexities related to these new treatments oftentimes cause great concern for the patients due to the general uncertainty or lack of understanding related to these new procedures.

As a nonlimiting example, ostomy surgery can oftentimes be a terrifying experience for patients. In fact, many patients oftentimes are not aware of the procedures related to ostomy surgery and the aftereffects related thereto. However, ostomy surgery, as well as many other medical treatments, may improve the quality of a patient's life, decrease mortality and morbidity, and in some cases, prevent serious disease.

Continuing with this nonlimiting example, the terms ostomy and stoma are general terms that are often used interchangeably, even though they have unlike meanings. An ostomy refers to the surgically created opening in the body for the excretion of bodily waste. A stoma is the actual end of the ureter or small or large bowel that is seen protruding through the wall of the abdomen.

A common type of ostomy is a colostomy, which is a surgically created opening in the abdomen through which a small portion of the colon, also known as the large bowel, is brought to the surface of the skin. This procedure may be performed by making an incision in the abdomen. The bowel resection, removal, or repair is performed through the incision, as needed.

After a colostomy surgery, stool may pass through the new opening (stoma) so that waste may pass directly out of the body, thereby bypassing a diseased or damaged section of the colon. In some patients, this diseased section may be removed. Nevertheless, a drainage bag or pouch may be attached to the skin around the stoma such that stool drains into the pouch.

A colostomy may be temporary or permanent. A temporary colostomy may be used when the part of the colon—usually the lower section—is allowed to heal after trauma or surgery or other similar situations. After the colon has healed, the colostomy may be reversed, thereby returning the bowel function to normal.

A permanent colostomy, also known as an end colostomy, is implemented for some conditions, such as colon cancer. This type of surgery is commonly used when the rectum needs to be removed because of disease. Most of the colon may be removed, and the remaining portion may be used to create a stoma.

As related to colostomies, there are generally various types of colostomies, which are associated with the portion of the bowel where the colostomy is located. A sigmoid or descending colostomy involves bringing the descending or sigmoid colon to the surface of the abdomen. This type of ostomy surgery is usually located on the lower left side of the abdomen.

A transverse colostomy is a surgical opening created in the transverse colon, resulting in one or two openings. The transverse colostomy is located in the upper abdomen, middle or right side in most instances.

A loop colostomy is a procedure that is usually created in the transverse colon. This is one stoma with two openings. One opening discharges stool, while a second opening discharges mucus.

In addition to colostomies, another type of ostomy is an ileostomy. An ileostomy is a surgically created opening in the small intestine, usually at the end of the ileum. The small intestine passes through the abdominal wall to form a stoma. Ileostomies may be temporary or permanent, and may involve removal of all or part of the entire colon.

Yet another type of ostomy is a urostomy. A urostomy is a surgical procedure that diverts urine away from a diseased or defective bladder. In ileal conduit is a common type of urostomy procedure. Either a section at the end of the small bowel (ileum) or at the beginning of the large intestine (cecum) is surgically removed and relocated as a passageway (conduit) for urine to pass from the kidneys to the outside of the body through a stoma. This type of procedure may or may not involve removal of the diseased bladder.

Regardless of the type of ostomy surgery, many patients may find it confusing to understand the procedures involved in their surgery. As a nonlimiting example, a patient undergoing an ostomy procedure may have difficulty understanding the various elements involved. The underlying condition that leads to an ostomy may very well have an effect on the patient's emotional, psychological, and physical recovery from the surgery. Changes in body image, lifestyle, and one's sexuality relating from this and other similar types of surgeries may cause great anxiety in the patient prior to undergoing the procedure. Thus, it may not only be difficult for the patient to understand the surgical procedure involved, but it may also be difficult for the patient to comprehend the effects that the surgery will have on the patient's life thereafter.

Consequently, many medical providers are attempting to educate a patient prior to surgical procedures, so as to minimize any uncertainties and misunderstandings about the procedures themselves and the effects thereafter. While these efforts can be beneficial, oftentimes patients are simply unable to fully appreciate the procedures and aftereffects involved in such surgeries as well as how the surgeries. As a nonlimiting example, a patient that has been under anesthesia prior to undergoing an ostomy surgery may still be dazed and confused so as to not fully comprehend the aspects of the pending surgery. As an additional nonlimiting example, elderly patients, due to reasons of poor hearing and memory retention problems, may not fully understand such surgical procedures as well. As an additional nonlimiting example, younger patients, such as a teenager, may experience great anxiety with the thought of having stool leaking from their abdomen as a result of an ostomy procedure and may have great difficulty in imagining such a lifestyle change. As another nonlimiting example, patients with language or educational barriers may not fully comprehend and understand explanations related to surgeries as explained by physicians and attending nurses prior to undergoing such procedures.

In an attempt to better educate patients prior to the performance of such surgical procedures, physicians have sought several solutions to better explain the procedures and their effects prior to the patient undergoing surgery. In addition to explanations, which may be laced with medical terms beyond the understanding of a lay patient, physicians and nurses may oftentimes rely on charts, books, and other medical references so as to explain the surgical procedure prior to going into the operating room. However, such charts and other references are generally not tailored for the wide range of patients that may be diagnosed for such surgical procedures. As a result, these displays and aids are oftentimes not well suited for a particular patient. As a result, explaining the procedure remains difficult and of little benefit.

Further, charts, textbooks, and other visual aids oftentimes require a nurse or other physician having to hold or otherwise direct their attention to these devices. These aids and props generally place the explaining physician or nurse at a localized area rather than permitting movement to better illustrate a certain aspect of the surgery. Thus, these explanatory aids include limitations and encumbrances for educating patients about the surgical procedures which they are scheduled to undergo.

As a result, a heretofore unaddressed need exists to address the aforementioned deficiencies and inadequacies described above.

DESCRIPTION OF THE DRAWINGS

Many aspects of the invention can be better understood with reference to the following drawings. The components in the drawings are not necessarily to scale, emphasis instead being placed upon clearly illustrating the principals of the present invention. Moreover, in the drawings, like reference numerals designate corresponding parts throughout the several views.

DETAILED DESCRIPTION

In addition to the drawings discussed above, this description describes one or more embodiments as illustrated in the above-referenced drawings. However, there is no intent to limit this disclosure to a single embodiment or embodiments that are disclosed herein. On the contrary, the intent is to cover all alternatives, modifications, and equivalents included within the spirit and scope of this disclosure and as defined by the appended claims.

An anatomical apron configured for illustrating an ostomy surgical procedure is disclosed herein. The apron may be worn by a nurse or physician who may demonstrate a surgical procedure by referencing the apron. The apron includes a body portion having a neck loop attached thereto that is configured to loop around a person's neck so that the body portion covers a frontal area of the person's body. The apron includes one or more pieces of material fashioned as human body organs fastened to the apron body. A first flap is attached to the apron body and configured to cover a portion of the one or more pieces of material fashioned as body organs, wherein the first flap may be fastened in a covered position. The apron also includes one or more slits positioned in the first flap configured such that one or more of the pieces of material fashioned as bodily organs may be routed through so as to illustrate a surgical procedure.

Figure 1:
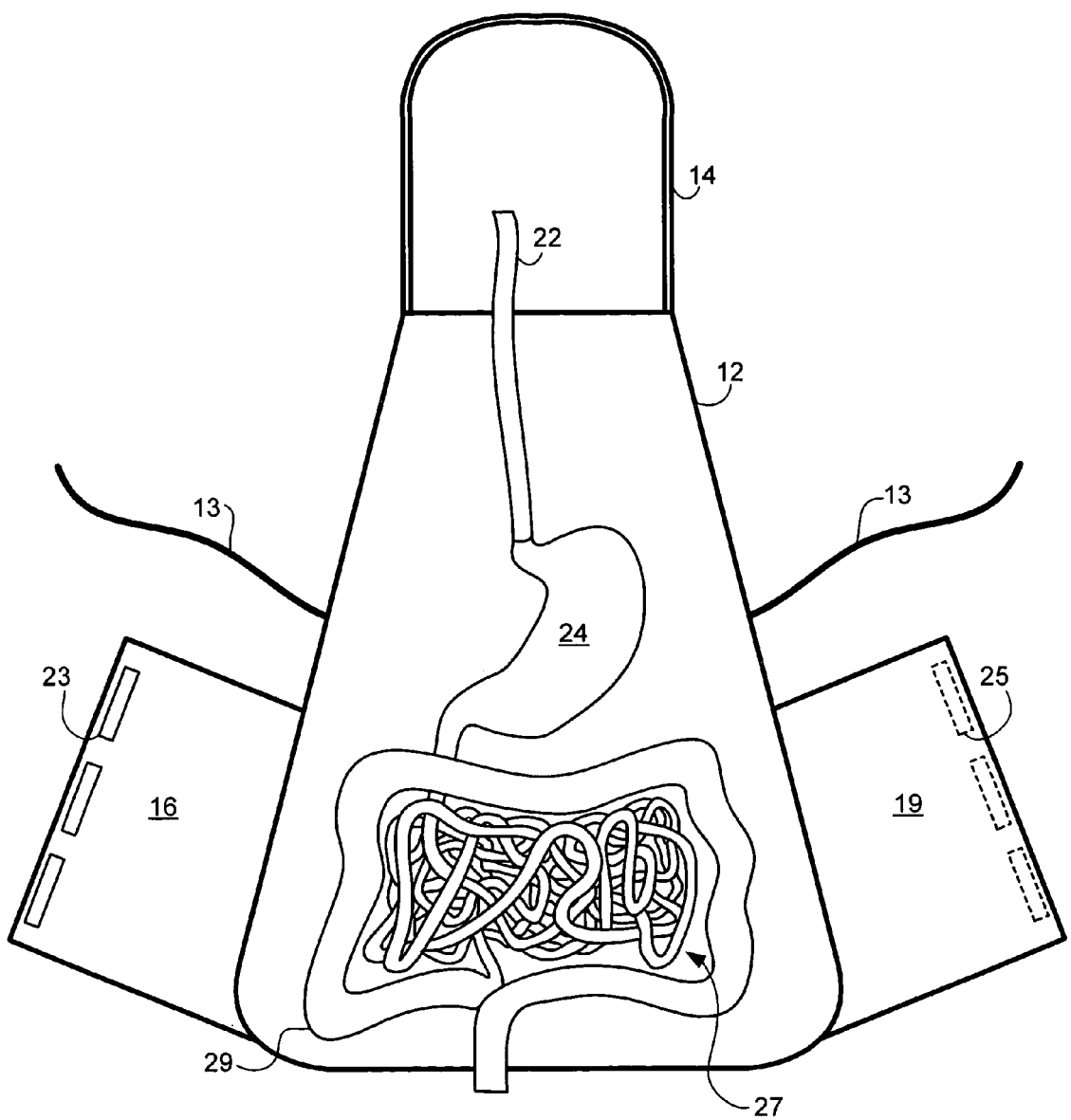
FIG. 1 is a diagram of the anatomical apron of this disclosure depicting a human gastrointestinal tract.

FIG. 1 is a diagram of the anatomical apron 10 of this disclosure, depicting a human gastrointestinal tract. In this diagram, anatomical apron 10 is constructed of a body portion 12 and a neck loop 14 as one of ordinary skill in the art would commonly know in association with apron construction. Neck loop 14 may be inserted around a wearer's head such that apron body 12 hangs over a frontal portion of a wearer's body, which may be a physician, nurse, or other individual explaining the surgical procedure depicting on the front of the apron 10. As is evident to one of ordinary skill in the art, ties 13 may be coupled on either side of body portion 12 so that a wearer may secure the apron 10 around the wearer's person.

In this nonlimiting example, body portion 12 of anatomical apron 10 depicts a gastrointestinal tract comprising an esophagus 22 coupled to stomach 24. Stomach 24 is thereafter coupled to small intestine 27 which terminates into colon 29.

Each of these body parts may be placed on the apron in any fashion, which itself may be constructed of any fabric, as is evident to one of ordinary skill in the art. Thus, as a nonlimiting example, apron 10 may be of a cotton construction and body parts, such as stomach 24, may be fashioned in a felt or other similar material. In one embodiment among others, esophagus 22, stomach 24, small intestine 27, and colon 27 may be fashioned in materials having a general color comparable to the actual organs in the human body. Nevertheless, each of these organ representations may be sewn, glued, or otherwise fastened to the body portion 12 of anatomical apron 10. A portion of the esophagus 22 may actually be configured to extend above the body portion 12 so as to be placed upon the neck of the person wearing the anatomical apron 10 for anatomical correctness. Stated another way, the wearer may show the esophagus 22 extending beyond the top portion of the body up to the wearer's neck.

In explaining the function of these organs, the wearer of anatomical apron 10 may use both hands to depict the function of the esophagus 22, stomach 24, small intestine 27, and colon 29, with freedom of movement while doing so. As a nonlimiting example, one or more of these body part representations may be configured to be removed from the body portion 12 of anatomical apron 10 so as to better depict or illustrate an aspect of a surgical procedure to be performed related to these bodily organs.

Flaps 16 and 19 positioned on either side of body portion 12 of anatomical apron 10 may be fastened to body portion 12 in any method, as is evident to one of ordinary skill in the art. More specifically, flaps 16 and 19 may contain fasteners 23 (on flap 16) and 25 (on flap 19, which may actually be positioned on the opposite surface of flap 19). Fasteners 23 and 25 may comprise any fastening means known to one of ordinary skill in the art. Such nonlimiting examples include: VELCRO®, snaps, zippers, buttons, ties, clips, adhesives, magnets, cords, or any other comparable fastening means. As displayed in FIG. 1, fasteners 23 and 25 may be complimentary VELCRO® strips to hold flaps 16 and 19 in place.

As discussed in more detail below, flaps 16 and 19 may represent an abdominal wall or epidermis layer that would otherwise cover the small intestine 27 and colon 29, as depicted in FIG. 1. In the illustration of FIG. 1, however, flaps 16 and 19 are in an open position so that the patient may easily view the gastrointestinal tract as described above. In this position, a nurse or physician may use both hands to identify and describe each organ on apron body 12, especially as it may relate to a pending surgical procedure.

However, flaps 16 and 19 may be configured in different sizes than as shown in FIG. 1. One of ordinary skill would understand that flaps 16 and 19 could actually be a single flap attached to body portion 12 on one side or perhaps configured larger than as shown in FIG. 1 so as to cover a greater portion of body portion 12.

Figure 2:
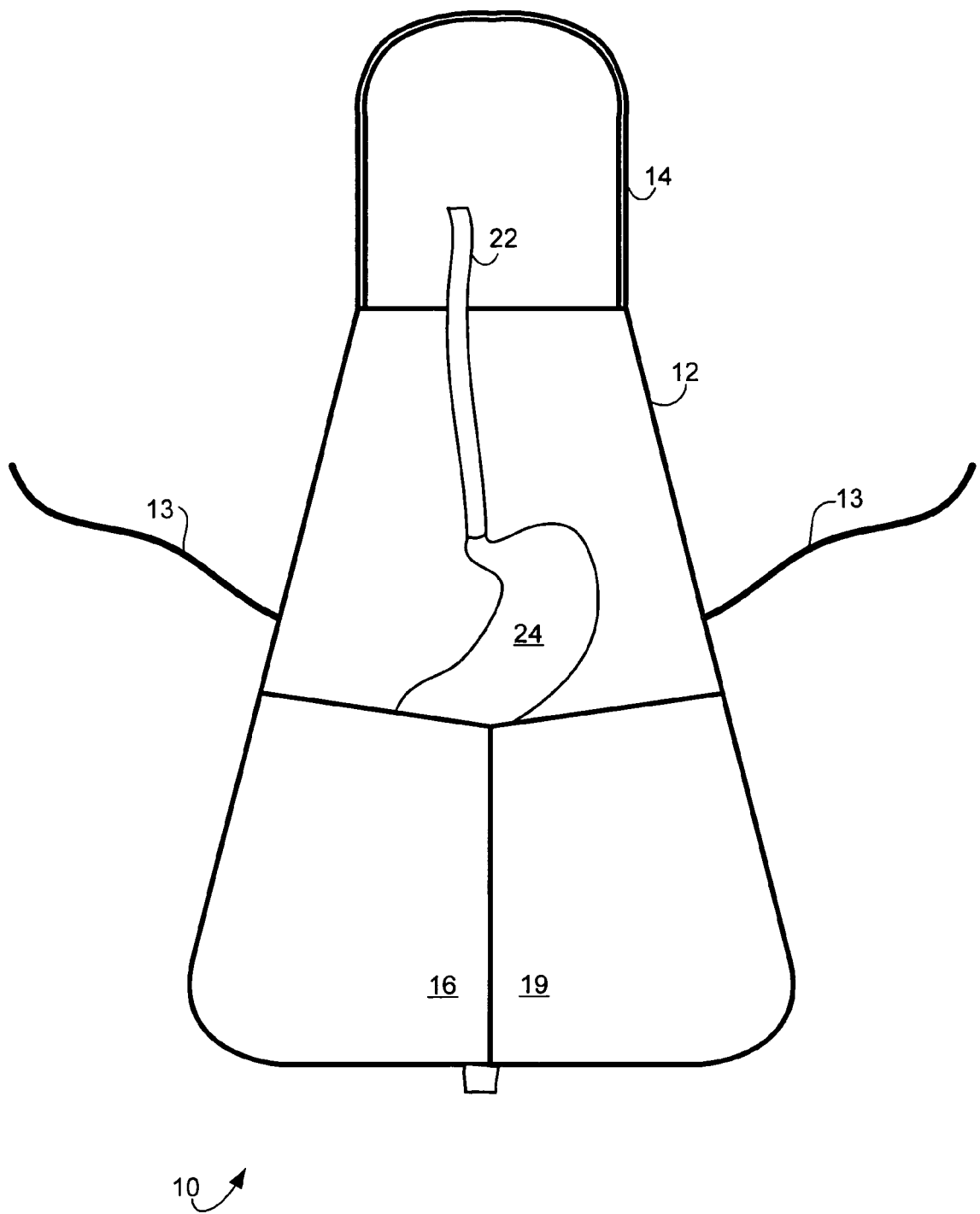
FIG. 2 is a diagram of the anatomical apron of FIG. 1 with two flaps covering the gastrointestinal tract of FIG. 1.

FIG. 2 is a diagram of the anatomical apron 10 of FIG. 1 with flaps 16 and 19 in a closed position. As illustrated in FIG. 2, flaps 16 and 19 obscure the patient's view to small intestine 27 and colon 29, as depicted in FIG. 1. In respect to illustrating a surgical procedure, flaps 16 and 19 may represent the outer abdominal wall that would otherwise cover the small intestine and colon of the patient. Flaps 16 and 19 may fasten together in a closed fashion, as shown in FIG. 2, in any method evident to one in ordinary skill in the art, such as VELCRO®, snaps, zippers, buttons, ties, clips, adhesives, magnets, cords, or any other comparable fastening means.

Figure 3:
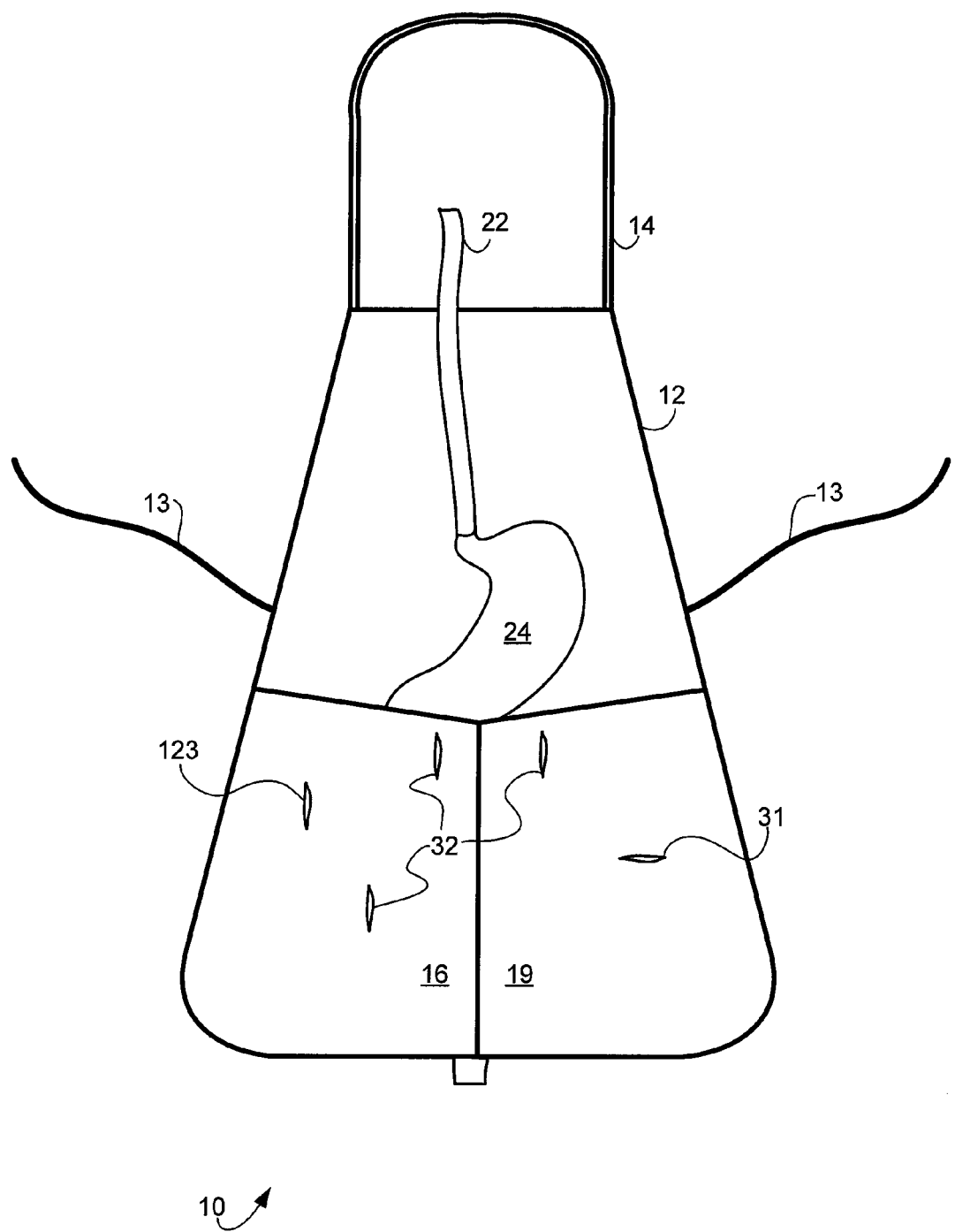
FIG. 3 is a diagram of the anatomical apron of FIG. 2 depicting the placement of slits on the outer surface of the adjustable flaps.

FIG. 3 is a diagram of the anatomical apron 10 of FIGS. 1 and 2 with flaps 16 and 19 in a closed position. In this nonlimiting example, flaps 16 and 19 include slits 123 and 31 positioned in the approximate locations where the surgical procedure related to the ostomies described above may take place. As discussed in more detail above, certain ostomy procedures involve incisions in different parts of the gastrointestinal area of a patient for bringing either the small intestine or a portion of the colon beyond the abdominal wall. Thus, the anatomical apron 10 of FIG. 3 may be used to illustrate the approximate location of the incisions to the patient to illustrate the relatively small size of the incision and the approximate locality thereof. As a nonlimiting example, a physician may use slits 123 and 31 to calm patient concerns in regard to undergoing the surgical procedure, and more specifically to being cut by a surgical knife.

One of ordinary skill would also know that additional slits 32 may be configured in flaps 16 and 19 for demonstrating other surgical procedures. So the number and position of the slits 123, 31, and 32 are not limited to the configurations shown in the figures and as described herein.

Figure 4:
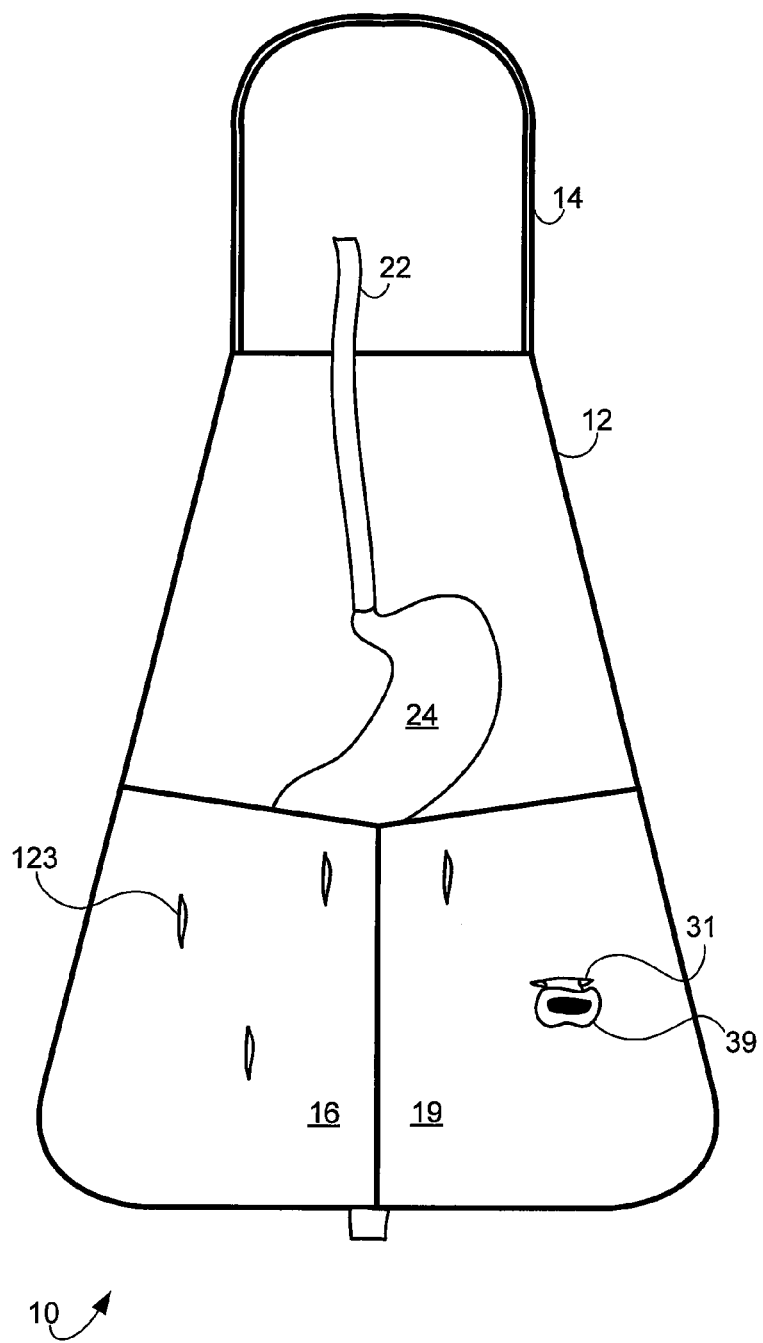
FIG. 4 is a diagram of the anatomical apron of FIG. 1 depicting the placement of a stoma on the outer surface of the adjustable flaps.

FIG. 4 is a diagram of the anatomical apron of FIGS. 1-3 with flaps 16 and 19 in a closed position. In this diagram of FIG. 4, the actual stoma is illustrated as a portion of the colon 39 is brought through slit 31. As described above, when a portion of a colon 29 (FIG. 1) may be raised through the abdominal wall incision, a stoma is created such that a pouch may be thereafter coupled to the created stoma. Thus, in illustrating this surgical procedure, a nurse or physician may illustrate the approximate location of the incision (slit 31) and thereafter remove a portion of the colon 29, which may be also sewn or otherwise attached to the body of apron 10. Stated another way, in this nonlimiting example, the colon portion 39 may be a piece of material coupled to apron body 12 such that when flaps 16 and 19 are closed, colon portion 39 may be extracted through slit 31 to illustrate how the surgical procedure may transpire. In this nonlimiting example, the embodiment disclosed therein may be a sigmoid or a descending colostomy, which involves bringing the descending colon 29 through the abdominal wall.

Slit 24 in FIG. 4 may be utilized to depict or illustrate a transverse colostomy wherein a piece of the transverse colon 29 is brought through an opening in the abdominal wall. Thus, as a nonlimiting example, in FIG. 1 a piece of material may be fastened to the body 12 of anatomical apron 10 so that it may be routed through slit 24 to show the approximate location of the stoma.

One of ordinary skill in the art would understand that one or more slits, such as slit 24 and/or 31, may be fastened to flaps 16 and 19 which illustrate the abdominal wall of the patient that receives the incision for the surgery. In placing one or more slits in flaps 16 and 19, other surgical procedures, as described above, may be illustrated with pieces of material attached to the body 12 of anatomical apron 10. Thus, one of ordinary skill in the art would understand that this disclosure is not limited to a particular type of ostomy but is instead configured with the various human bodily organs for the particular surgery to be illustrated or explained.

As a nonlimiting example, anatomical apron 10 may be reconfigured with different bodily elements to illustrate a different surgical procedure, as similarly described above. In each case, the physician or nurse wearing the anatomical apron 10 may more thoroughly describe and explain the actual surgical procedure to be performed, therefore allaying any fears or concerns that the patient may gave prior to undergoing the surgical procedure.

The various organs constructed of cotton, felt, or other materials may be sewn or otherwise fastened to the apron body 12 in approximate realistic proportion to the actual human body so as to provide a reference point for the patient viewing the illustration. Thus, as related to the ostomy procedures described above, the anatomical apron 10 described herein may visually communicate to the patient the approximate opening in the abdominal wall and the approximate location of any pouch that may be coupled to the stoma created through the procedure. So in addition to verbal instruction or explanation prior to performing a surgical procedure, a patient may visually see how the particular surgery will be performed and the approximate postoperative effects related thereto.

Figure 5:
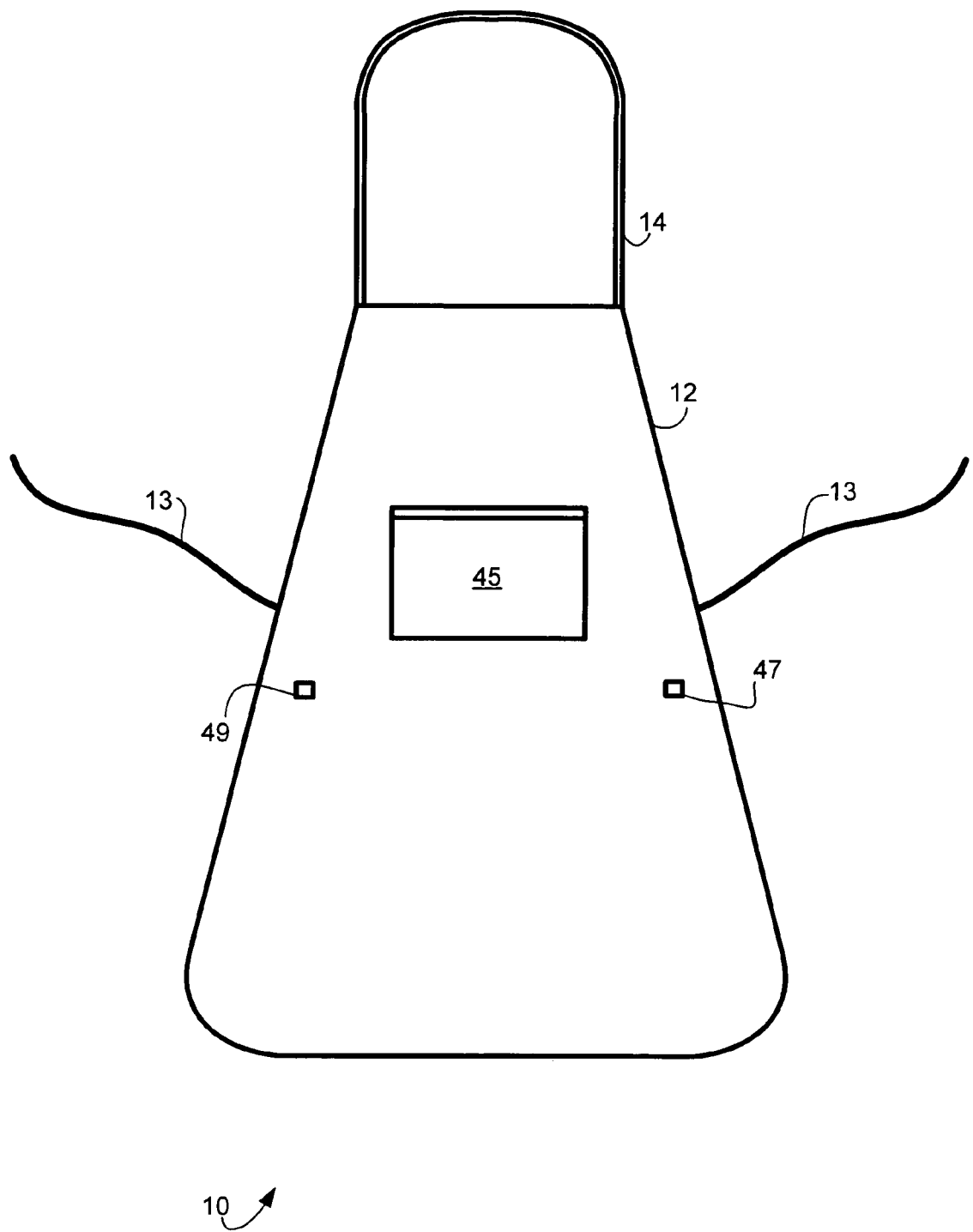
FIG. 5 is a diagram of a reverse side of the anatomical apron of FIG. 1.

FIG. 5 is a diagram of a reverse side of the anatomical apron 10 of FIG. 1. Pouch 45 may be positioned on the reverse side of body portion 12 from the organs (22, 24, 27, and 29) of FIG. 1. Pouch 45 may be used for storing one or more of the fashioned body organs used for demonstrating a surgical procedure.

As a nonlimiting example, pouch 45 may contain a piece of cloth or other material fashioned to look like a part of the colon 29. In demonstrating a colostomy, the wearer may collect the colon-fashioned cloth and attach it to the front side of body portion 12, as described above. Attaching means, such as VELCRO®, may be used to attach the colon-fashioned cloth to colon 29 so that another portion of the cloth may be routed through slit 31 of flap 19. Because apron 10 may be configured for a variety of surgical procedures, pouch 45 may be configured to contain a number of organ-shaped materials. One of ordinary skill would also understand that multiple pouches 45 may be attached to the reverse side of body portion 12 to store body organs related to separate surgical procedures.

The reverse side of body portion 12 may also contain fasteners 47, and 49, which may be utilized to fasten ties 13. Thus, fasteners 47 and 49 may be any type of fastening devices, as is evident to one of ordinary skill in the art.

As indicated above, the body organs displayed on body portion 12 may vary according to the particular surgical procedure demonstrated. Thus, in one nonlimiting example, the body organs of FIG. 1 are detachable from body portion 12 via fastening means, such as the following nonlimiting examples: VELCRO®, snaps, buttons, ties, clips, adhesives, magnets, cords, etc.

Figure 6:
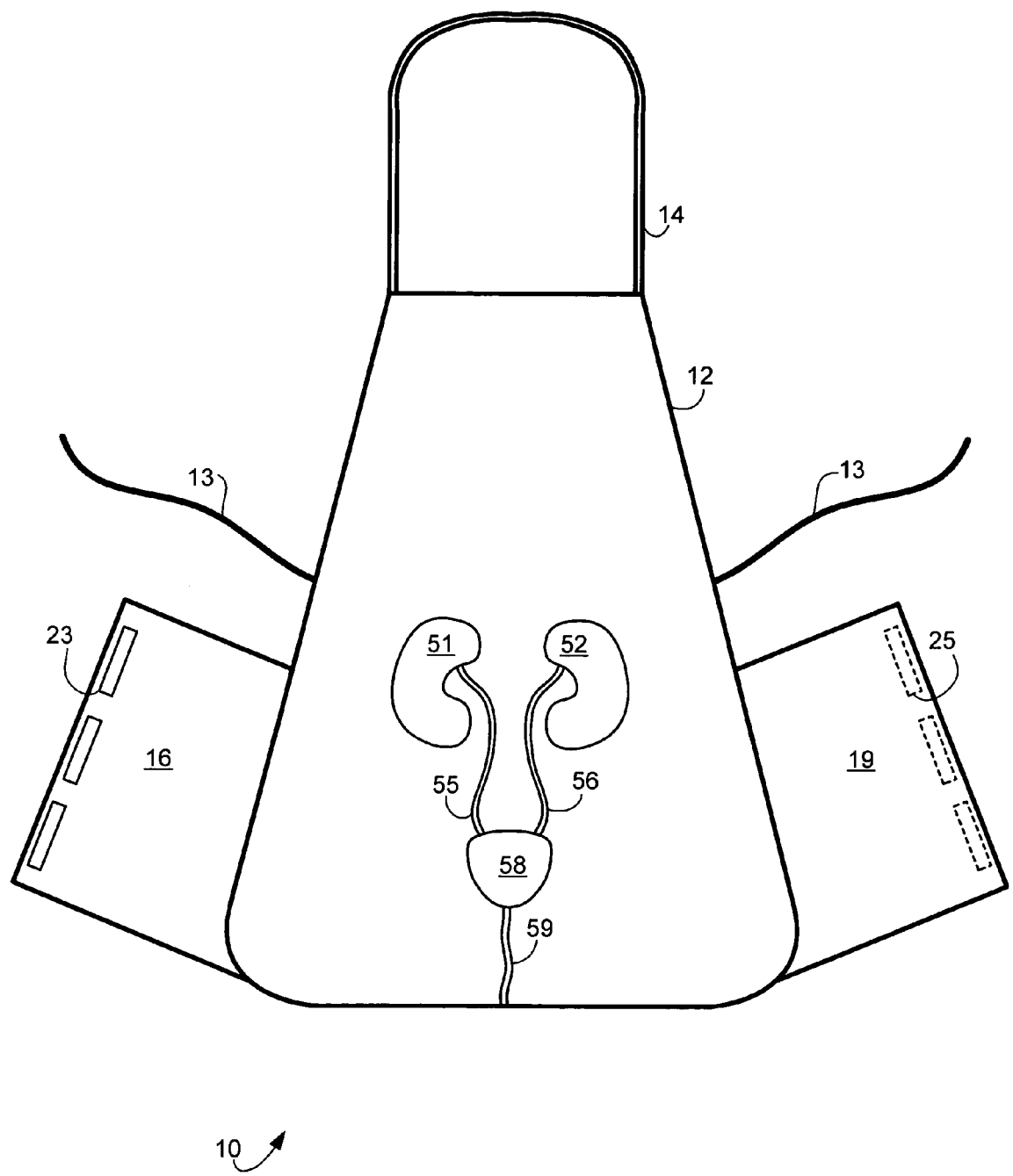
FIG. 6 is a diagram of a nonlimiting exemplary display of body organs that are different than the nonlimiting exemplary display of FIG. 1.

FIG. 6 is a diagram of a nonlimiting exemplary display of body organs that are different than the nonlimiting exemplary display of FIG. 1. This nonlimiting example depicts a human urinary tract for demonstrating a urostomy, as described above. This configuration may be used, more specifically, for demonstrating an ileal conduit.

Apron 10 in FIG. 6 includes kidneys 51, 52; ureters 55, 56; urinary bladder 58, and urethra 59. As discussed above, an ileal conduit is a common type of urostomy procedure. Either a section at the end of the small bowel (ileum) or at the beginning of the large intestine (cecum) is surgically removed and relocated as a passageway (conduit) for urine to pass from the kidneys to the outside of the body through a stoma. Thus, appropriate cloth-shaped organs may be stored in pouch 45 (FIG. 5) so that a wearer may demonstrate this procedure consistent to as described above.

It should be emphasized that the above-described embodiments and nonlimiting examples are merely possible examples of implementations, merely set forth for a clear understanding of the principles disclosed herein. Many variations and modifications may be made to the above-described embodiment(s) and nonlimiting examples without departing substantially from the spirit and principles disclosed herein. All such modifications and variations are intended to be included herein within the scope of this disclosure and protected by the following claims.

I claim:

1. An anatomical apron configured for illustrating a surgical procedure, comprising:
   an apron body portion having a neck loop attached thereto configured to loop around a person's neck so that the body portion covers a frontal area of the person's body;
   one or more pieces of material fashioned as human body organs fastened to the apron body;
   a first flap attached to the apron body, the first flap extending laterally from the apron body, a first portion of the first flap being securely attached to the apron body at a first position, a second portion of the first flap configured for being removably secured to a second flap while the anatomical apron is worn, the second flap extending laterally from the apron body, the first flap being further configured to cover a portion of the one or more pieces of material fashioned as body organs when the second portion of the first flap is secured to the second flap; and
   one or more slits positioned in the first flap configured such that one or more of the pieces of material fashioned as human body organs may be routed from the apron body, through the first flap, so as to illustrate a surgical procedure.

2. The apron of claim 1, wherein the one or more pieces of material fashioned as human body organs are detachably fastened to the apron body.

3. The apron of claim 1, further comprising:
   the second flap attached to the apron body and configured to removably secure with the first flap in a central area of the apron body so as to conceal a portion of the one or more pieces of material fashioned as human body organs.

4. The apron of claim 3, further comprising:
   one or more slits positioned in the second flap configured such that one or more of the pieces of material fashioned as human body organs may be routed through so as to illustrate a surgical procedure.

5. The apron of claim 3, wherein the first and second flaps includes fastening means for holding the flaps in position so as to conceal a portion of the one or more pieces of material fashioned as human body organs.

6. The apron of claim 1, wherein a plurality of the one or more pieces of material fashioned as human body organs are configured to extend through the one or more slits.

7. The apron of claim 1, further comprising:
   a pouch positioned on a reverse side of the apron body from the one or more pieces of material fashioned as human body organs and configured to store one or more of the pieces of material fashioned as human body organs.

8. A tool for teaching procedures performed in a colostomy surgical procedure, comprising:
   an apron having a neck loop;
   a first material fastened to the apron having an appearance of a human esophagus;
   a second material fastened to the apron having an appearance of a human stomach;
   a third material fastened to the apron having an appearance of a small intestine;
   a fourth material fastened to the apron having an appearance of a colon;
   a first flap securely coupled to the apron at a first position, the first flap configured to extend laterally from the apron around a front portion of the apron so as to cover a portion of the second, third and fourth materials, the first flap configured to removably secure to a second flap while the apron is worn, the second flap extending laterally from the apron; and
   one or more slits in the one or more flaps configured such that a portion of the third or fourth material may be placed though the slit so as to illustrate a stomach.

9. The tool of claim 8, wherein each of the first, second, third, and fourth materials are colored comparably to the corresponding human body parts.

10. The anatomical apron of claim 1, wherein the neck loop is different than the first flap and the second flap.

11. The anatomical apron of claim 1, further comprising a first tie and a second tie, the first tie and the second tie secured to the body portion, the first tie and the second tie configured to removably secure the anatomical apron to the person's body when the anatomical apron is being worn.

12. The anatomical apron of claim 11, wherein the first tie and second tie are different than the first flap and the second flap.

13. The anatomical apron of claim 8, wherein the one or more flaps is configured such that a portion of the third or fourth material may be placed though the slit so as to illustrate a colon.

14. The anatomical apron of claim 8, further comprising a first tie and a second tie, the first tie and the second tie secured to the body portion, the first tie and the second tie configured to removably secure the anatomical apron to the person's body when the anatomical apron is being worn.

15. The anatomical apron of claim 14, wherein the first tie and second tie are different than the first flap and the second flap.

16. An anatomical apron configured for illustrating a surgical procedure, comprising:
- an apron body portion having a neck loop attached thereto configured to loop around a person's neck so that the body portion covers a frontal area of the person's body;
- one or more pieces of material fashioned as human body organs fastened to the apron body;
- a first flap attached to the apron body, the first flap extending laterally from the apron body, a first portion of the first flap being securely attached to the apron body at a first position; and
- a second flap attached to the apron body, the second flap extending laterally from the apron body, a first portion of the second flap being securely attached to the apron body at a first position,
- wherein a second portion of the first flap is configured for being removably secured to a second portion of the second flap while the anatomical apron is worn, the first flap being further configured to cover a portion of the one or more pieces of material fashioned as body organs when the second portion of the first flap is secured to the second flap.

17. The anatomical apron of claim 16, further comprising one or more slits positioned in the first flap configured such that one or more of the pieces of material fashioned as human body organs may be routed from the apron body, through the first flap, so as to illustrate a surgical procedure.

18. The anatomical apron of claim 16, wherein the neck loop is different than the first flap and the second flap.

19. The anatomical apron of claim 16, further comprising a first tie and a second tie, the first tie and the second tie secured to the body portion, the first tie and the second tie configured to removably secure the anatomical apron to the person's body when the anatomical apron is being worn.

20. The anatomical apron of claim 19, wherein the first tie and second tie are different than the first flap and the second flap.

* * * * *